(12) United States Patent
Shad et al.

(10) Patent No.: US 10,149,754 B2
(45) Date of Patent: Dec. 11, 2018

(54) SUTURING RING FOR PROSTHETIC HEART VALVES

(71) Applicants: Sujay Kumar Shad, New Delhi (IN); Rohan Shad Arora, New Delhi (IN)

(72) Inventors: Sujay Kumar Shad, New Delhi (IN); Rohan Shad Arora, New Delhi (IN)

( * ) Notice: Subject to any disclaimer, the term of this patent is extended or adjusted under 35 U.S.C. 154(b) by 27 days.

(21) Appl. No.: 15/146,075

(22) Filed: May 4, 2016

(65) Prior Publication Data

US 2017/0202664 A1 Jul. 20, 2017

(30) Foreign Application Priority Data

Jan. 20, 2016 (IN) .............................. 201611002178

(51) Int. Cl.
*A61F 2/24* (2006.01)

(52) U.S. Cl.
CPC .......... *A61F 2/2409* (2013.01); *A61F 2/2403* (2013.01); *A61F 2220/0008* (2013.01); *A61F 2230/0006* (2013.01); *A61F 2230/0013* (2013.01); *A61F 2250/0036* (2013.01); *A61F 2250/0039* (2013.01); *A61F 2250/0069* (2013.01)

(58) Field of Classification Search
CPC ........... A61F 2/04–2002/068; A61F 2230/001; A61F 2250/0036; A61F 2250/0039
See application file for complete search history.

(56) References Cited

U.S. PATENT DOCUMENTS

| | | | | |
|---|---|---|---|---|
| 3,824,629 A | * | 7/1974 | Shiley | A61F 2/2406 137/527.8 |
| 4,661,106 A | * | 4/1987 | Moll | A61F 2/2406 623/2.25 |
| 4,846,830 A | * | 7/1989 | Knoch | A61F 2/2409 623/2.22 |
| 5,449,385 A | * | 9/1995 | Religa | A61F 2/2412 623/2.19 |
| 2003/0109922 A1 | * | 6/2003 | Peterson | A61F 2/2409 623/2.17 |
| 2007/0027536 A1 | * | 2/2007 | Mihaljevic | A61F 2/2445 623/2.37 |
| 2007/0198048 A1 | * | 8/2007 | Behan | A61F 2/04 606/194 |

* cited by examiner

*Primary Examiner* — Thomas J Sweet
*Assistant Examiner* — Rebecca S Preston
(74) *Attorney, Agent, or Firm* — Workman Nydegger (57) ABSTRACT

The present subject matter describes a suturing ring for a prosthetic heart valve. The suturing ring has a variable annular thickness reducing continuously from a mid-circumferential plane of the suturing ring towards a top peripheral edge and a bottom peripheral edge of the suturing ring.

8 Claims, 6 Drawing Sheets

SUTURING RING FOR PROSTHETIC HEART VALVES

CROSS-REFERENCE TO RELATED APPLICATION

This application claims priority to and the benefit of Indian Patent Application No. 201611002178, filed Jan. 20, 2016, entitled SUTURING RING FOR PROSTHETIC HEART VALVES, the entire content of the above application is incorporated herein by reference in its entirety.

TECHNICAL FIELD

The present subject matter relates in general to suturing rings, and in particular to suturing rings for prosthetic heart valves.

BACKGROUND

Valves perform important physiological functions in a human heart by controlling the direction and volume of blood flow through the heart. Typically, there are four valves in the human heart, viz., tricuspid valve, pulmonic valve, mitral valve and aortic valve. These valves regulate and maintain the blood flow to and from the heart. The aortic and pulmonic valves regulate flow form the ventricles into the aorta and pulmonary arteries, respectively. The mitral and tricuspid valves regulate flow from the left and right atria, respectively, into the ventricles. The human heart can suffer from various valvular diseases, which then broadly progress to stenosis or insufficiency. This can further result in significant malfunctioning of the heart and may require replacement of a native/natural valve in the heart with an artificial heart valve, also called a prosthetic heart valve. The prosthetic heart valve, like a bioprosthetic or mechanical heart valve, can be implanted in the human heart to replicate the function of the natural heart valve.

BRIEF DESCRIPTION OF DRAWINGS

The detailed description is described with reference to the following figures. It should be noted that the description and figures are merely examples of the present subject matter and are not meant to represent the subject matter itself.

FIG. 1b illustrates a cross-sectional view of housing and fabric layer of the conventional prosthetic heart valve of FIG. 1a.

FIG. 2b illustrates a cross-sectional view of another conventional suturing ring for the conventional prosthetic heart valve of FIG. 2a.

DETAILED DESCRIPTION

Prosthetic heart valves, hereinafter interchangeably referred to as prosthetic valves, can be of different types such as, single leaflet valves, bi-leaflet valves, caged ball valves, and the like. Generally, a bi-leaflet prosthetic valve includes a valve housing, and two semicircular leaflets mounted within the valve housing through struts. The semicircular leaflets can rotate about the struts between an open position and a closed position to regulate flow of blood though the prosthetic valve. The prosthetic valve is stitched to native tissue when the prosthetic valve is implanted in the human body.

Figure 1A:
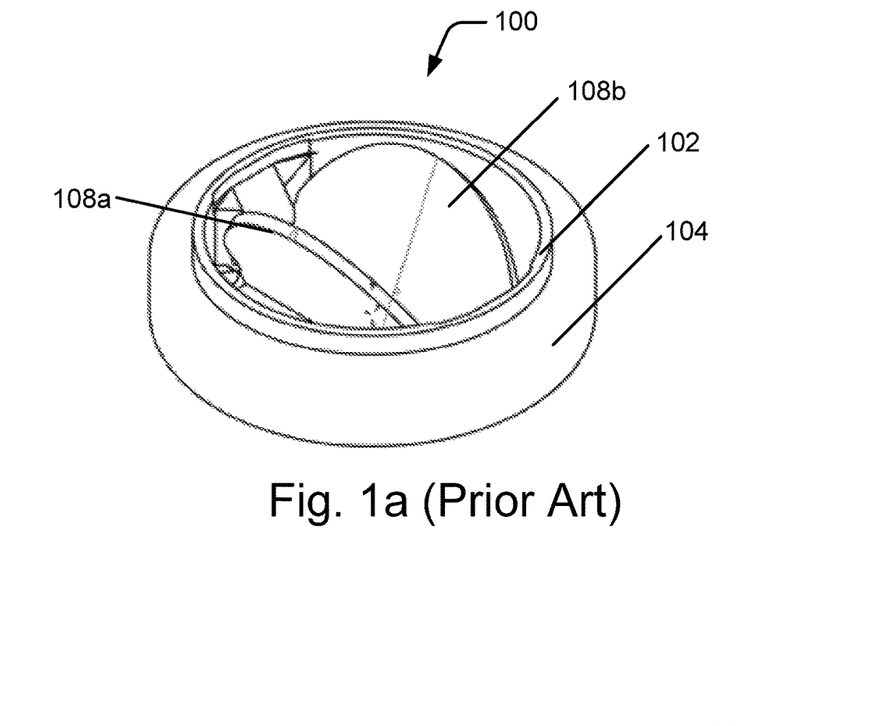
FIG. 1a illustrates a perspective view of a conventional prosthetic heart valve.
Figure 1B:
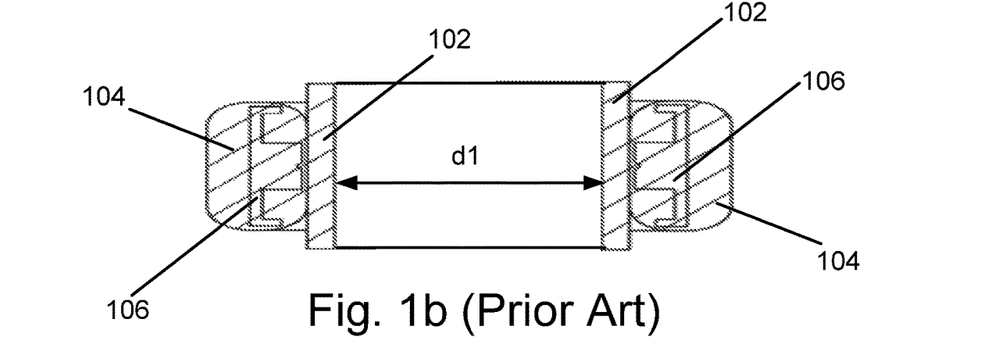

FIG. 1a illustrates a perspective view of a conventional prosthetic heart valve 100, hereinafter referred to as the valve 100. The valve 100 has a valve housing 102 and a fabric layer 104 circumferentially around the valve housing 102. FIG. 1b illustrates a cross-sectional view of the valve housing 102 and the fabric layer 104 of the valve 100. The fabric layer 104 includes fibers woven over a metal ring 106. The fabric layer 104 is secured to the valve housing 102. Two leaflets 108a and 108b, hereinafter collectively referred as leaflets 108, are mounted within the valve housing 102. The leaflets 108 open/close to regulate the flow of blood through the valve 100. At the time of an implant, the valve 100 may be stitched to the native tissue by using suture-threads which are passed though the fabric layer 104. The fabric layer 104 formed from woven fibers has a certain degree of porosity which allows growth of tissue and infectious seeding within the pores of the fabric layer 104 leading to medical conditions post implant of the valve 100.

The volume of blood flowing through the valve 100 depends on an effective orifice area of the valve 100 which in turn depends on an inner diameter d1, shown in FIG. 1b, of the valve housing 102. The effective orifice area increases with increase of the inner diameter d1 and decreases with decrease of the inner diameter d1. It may be noted that the fabric layer 104 of the valve 100 is required to have a substantial thickness in order to ensure proper stitching of the valve 100 with the native tissue. The valve housing 102 along with the fabric layer 104 generally has a thickness of about 4 mm. Since, the outer diameter of the valve 100 is substantially fixed, the thickness of the fabric layer 104 in addition to the thickness of the valve housing 102 puts a limitation on the extent to which the inner diameter d1 of the valve 100 can be increased. The smaller inner diameter d1 limits the effective orifice area of the valve 100 through which blood can flow, which may lead to a patient prosthesis mismatch creating a large pressure gradient of blood flowing through the valve 100. As a result the heart may have to work harder, which could cause heart muscles to become more muscular leading to a medical condition known as left ventricle hypertrophy.

Figure 2A:
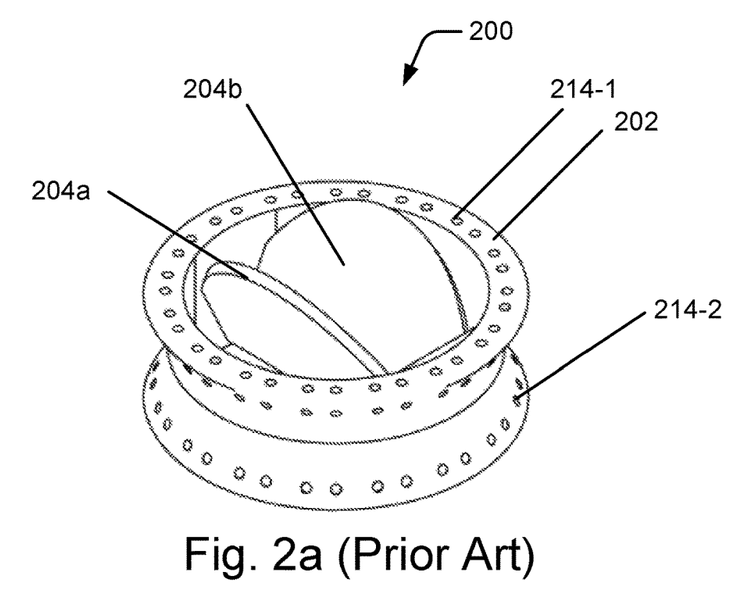
FIG. 2a illustrates a perspective view of another conventional prosthetic heart valve.
Figure 2B:
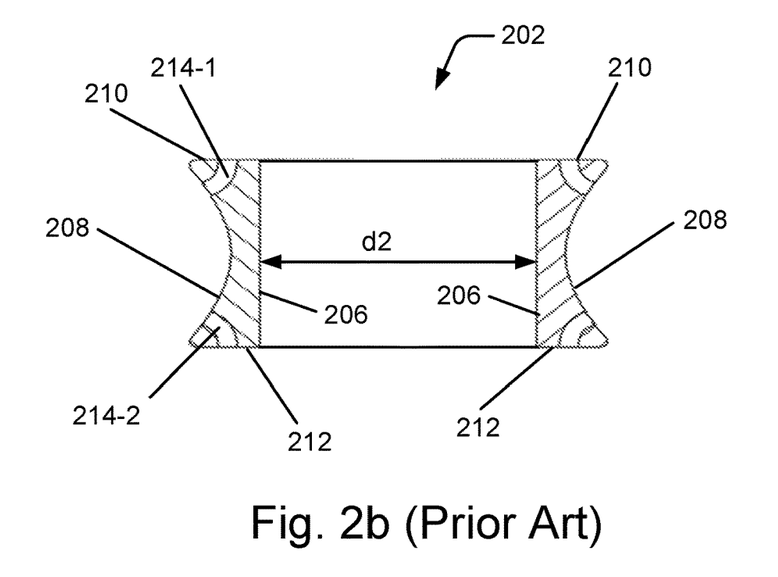

FIG. 2a illustrates a perspective view of another conventional prosthetic heart valve 200, hereinafter referred to as the valve 200. The valve 200 includes a conventional suturing ring 202 that functions as a valve housing. The conventional suturing ring 202 houses two leaflets 204a and 204b, hereinafter collectively referred as leaflets 204, which can rotate to regulate the flow of blood through the valve 200. FIG. 2b illustrates a cross-sectional view of the conventional suturing ring 202 for the valve 200 of FIG. 2a. The effective orifice area for the flow of blood through the valve 200 depends on an inner diameter d2 of the valve 200, as shown in FIG. 2b. The conventional suturing ring 202 has an annular cylindrical structure having an inner surface 206 and an outer surface 208. The inner surface 206 forms a boundary of the effective orifice area of the valve 200 and the outer surface 208 abuts with native tissue walls of the patient when the valve 200 is implanted in the patient's body. The outer surface 208 of the conventional suture ring 202 has a substantially curved profile while the inner surface 206 has a substantially planar profile. The conventional suturing ring 202 has a top end surface 210 and a bottom end surface 212. The top end surface 210 and the bottom end surface 212 meet the inner surface 206 at substantially 90 degrees thereby forming an L-shaped profile, as may be appreciated from FIG. 2b. The conventional suturing ring 202 also has suture-receiving passages 214-1, 214-2, hereinafter collectively referred to as suture-receiving passages 214. Suture-threads are passed through the suture-receiving passages 214 to stitch the valve 200 with the native tissue.

Since, the valve 200 eliminates the use of a fabric layer for stitching the valve 200 to the native tissue, chances of tissue growth and infectious seeding of the fabric layer are substantially reduced. Also, as there is no fabric layer, the inner diameter d2 of the valve 200 may be increased beyond the inner diameter d1 of the valve 100. Thus, the effective orifice area of the valve 200 through which blood may flow is greater as compared to the effective orifice area of the valve 100.

However, due to the planar surface profiles of the inner surface 206, the top end surface 210 and the bottom end surface 212 in the conventional suturing ring 202 a substantial non-uniformity in the flow path of blood flowing through the valve 200 when implanted in a human heart is introduced. Particularly, the L-shaped profile formed by the top end surface 210 and the inner surface 206 and by the bottom end surface 212 and the inner surface 206 introduces an abrupt obstruction in the flow path of the blood. The abrupt obstruction in the flow path creates substantial turbulence in the flow of blood through the valve 200, particularly at faces where blood enters and leaves the valve 200. The turbulence in the flow of blood through the valve 200 may result in medical complications such as, thrombosis, and may contribute to pannus formation, and the like, in the patient.

Further, each of the suture-receiving passages 214 in the conventional suturing ring 202 has a pre-defined diameter to allow passing of a surgical needle and a suture-thread for stitching the prosthetic valve to the native tissue. Generally, in the conventional suturing ring 202, the suture-receiving passages 214 are fabricated by drilling through-holes of the pre-defined diameter from the top end surface 210 to the outer surface 208 and from the bottom end surface 212 to the outer surface 208. Since the working dimensions of the conventional suturing ring 202 is of the order of a few millimeters, fabrication of suture-receiving passages 214 in the conventional suturing ring 202 from the top end surface 210 to the outer surface 208 and from the bottom end surface 212 to the outer surface 208 is difficult. In addition, during the fabrication of the suture-receiving passages 214 by drilling of through-holes there are chances of fracturing or damaging the conventional suturing ring 202, particularly at the top end surface 210 and the bottom end surface 212. Fracturing of the conventional suturing ring 202 at the region of the suture-receiving passages 214 may lead to valve instability, paravalvular regurgitation, and increases the risk of embolization of the valve 200 or fragments of the valve housing.

To avoid such fractures or damages, a substantial thickness between the inner surface 206 and the outer surface 208 is to be maintained at the top end surface 210 and the bottom end surface 212 of the conventional suturing ring 202. Since the outer diameter of the conventional suturing ring 202 is substantially fixed, the thickness between the inner surface 206 and the outer surface 208 at the top end surface 210 and the bottom end surface 212 places a limitation on the extent to which the inner diameter d2 of the conventional suturing ring 202 can be increased. A smaller inner diameter of the conventional suturing ring 202 limits the effective orifice area for the flow of blood through the valve 200, which may lead to a patient prosthesis mismatch. A severe mismatch can increase the chances of mortality by a factor of 10 in the long run. Also, the limited effective orifice area for flow of blood through the valve 200 may pose risks of medical conditions, such as left ventricle hypertrophy, especially in smaller hearts.

The present subject matter describes suturing rings for a prosthetic heart valve in which turbulence in the flow of blood is substantially reduced as compared to the turbulence in the flow of blood through the valve 100 and the valve 200. Also, the suturing rings of the present subject matter enable easy fabrication of suture-receiving passages while providing a larger effective orifice area for flow of blood through the prosthetic valve in comparison to the effective orifice area of the valve 100 and the valve 200.

In an example implementation, the suturing ring of the present subject matter has a variable annular thickness. The annular thickness of the suturing ring reduces continuously from a mid-circumferential plane towards a top peripheral edge and a bottom peripheral edge of the suturing ring. The suturing ring has an inner surface and an outer surface meeting at the top peripheral edge and the bottom peripheral edge, where the inner surface has a continuously increasing slope from the mid-circumferential plane towards the top peripheral edge and the bottom peripheral edge. The continuously reducing annular thickness and the continuously increasing slope of the inner surface of the suturing ring of the present subject matter eliminates the L-shaped profile otherwise existing in the conventional suturing ring 202 and provides a substantially smooth passage to the flow of blood through the prosthetic valve, particularly at the entry and exit faces of the prosthetic valve. The gradually sloping inner surface facilitates in substantial reduction in the turbulence in the flow of blood through the prosthetic valve. The reduced turbulence diminishes chances of platelet activation in the blood flowing through the prosthetic valve according to an example implementation of the present subject matter, and thereby minimizes chances of medical complications, such as thrombus formation and subsequent leaflet dysfunction, and hemolytic anemia. The reduced risk of thrombosis may further lead to a reduced need for medical anticoagulation therapy, which increases the quality of the life for the patient.

Further, in an example implementation, the suturing ring of the present subject matter has suture-receiving passages that pass from the inner surface to the outer surface of the suturing ring. Since the suture-receiving passages in the suturing ring of the present subject matter are between the inner surface and the outer surface and not between the top/bottom end surface and the outer surface as in the conventional suturing ring 202, the suture-receiving passages are easier to fabricate and the chances of fracturing or damaging the suturing ring are reduced.

Further, the design of the suturing ring of the present subject matter and the suture-receiving passages from the inner surface to the outer surface enables reduction in the thickness between the inner and outer surfaces of the suturing ring. This allows a valve employing the suturing ring of the present subject matter to have a larger inner diameter than the inner diameter of the valve 100 and the valve 200. The larger inner diameter results in increasing the effective orifice area of the prosthetic valve that effectuates an increase in the volume of blood flow through the prosthetic valve thereby minimizing the chances of patient prosthesis mismatch in even the smallest hearts.

The above mentioned implementations are further described herein with reference to the accompanying figures. It should be noted that the description and figures relate to exemplary implementations, and should not be construed as a limitation to the present subject matter. It is also to be understood that various arrangements may be devised that, although not explicitly described or shown herein, embody the principles of the present subject matter. Moreover, all statements herein reciting principles, aspects, and embodiments of the present subject matter, as well as specific examples, are intended to encompass equivalents thereof.

Figure 3:
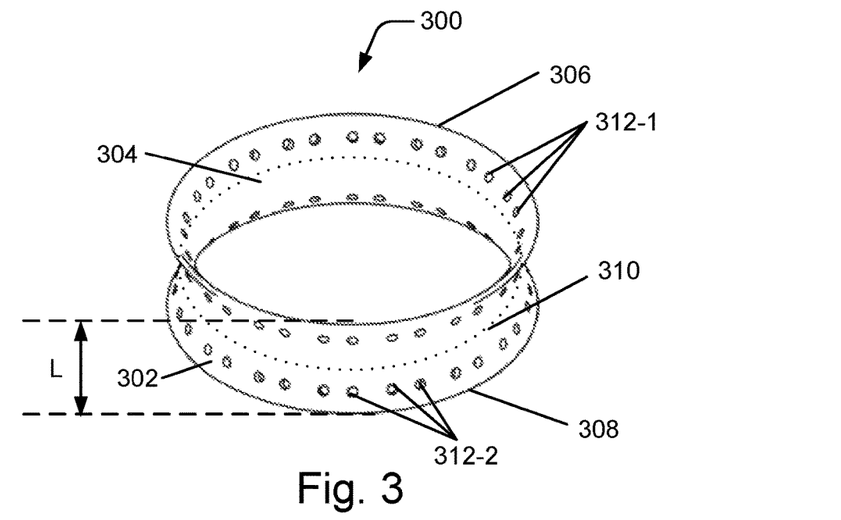
FIG. 3 illustrates a perspective view of a suturing ring for a prosthetic heart valve, in accordance with an example implementation of the present subject matter.

FIG. 3 illustrates a perspective view of a suturing ring 300 for a prosthetic valve, in accordance with an example implementation of the present subject matter. In an example implementation, the suturing ring 300 may form a valve housing of the prosthetic valve. The suturing ring 300 has an annular structure having an outer surface 302 and an inner surface 304. When the prosthetic valve is surgically implanted within the human body, the outer surface 302 abuts native tissues in the human body and the inner surface 304 comes in contact with blood flowing through the prosthetic valve.

As shown in FIG. 3, the outer surface 302 meets the inner surface 304 at a top peripheral edge 306 and a bottom peripheral edge 308 of the suturing ring 300. In an example implementation, the prosthetic valve may be a prosthetic aortic valve which may be surgically implanted to replace a natural aortic valve located between the aorta and the left ventricle of a human heart. Thus, in the example implementation, the top peripheral edge 306 may be understood as the edge where the outer surface 302 meets the inner surface 304 on the aortic side of the prosthetic aortic valve and the bottom peripheral edge 308 may be understood as the edge where the outer surface 302 meets the inner surface 304 on the left ventricular side. The top peripheral edge 306 and the bottom peripheral edge 308 may be separated by a linear distance denoted by L in FIG. 3. The linear distance L may be understood to be the shortest distance between the top peripheral edge 306 and the bottom peripheral edge 308. The linear distance L maybe in a range from about 4.5 mm to about 10.5 mm.

FIG. 3 depicts a boundary 310 of a mid-circumferential plane of the suturing ring 300. The boundary 310 of the mid-circumferential plane may be understood to be boundary of a plane passing through the suturing ring 300 at which the annular thickness of the suturing ring 300 is maximum.

Figure 4:
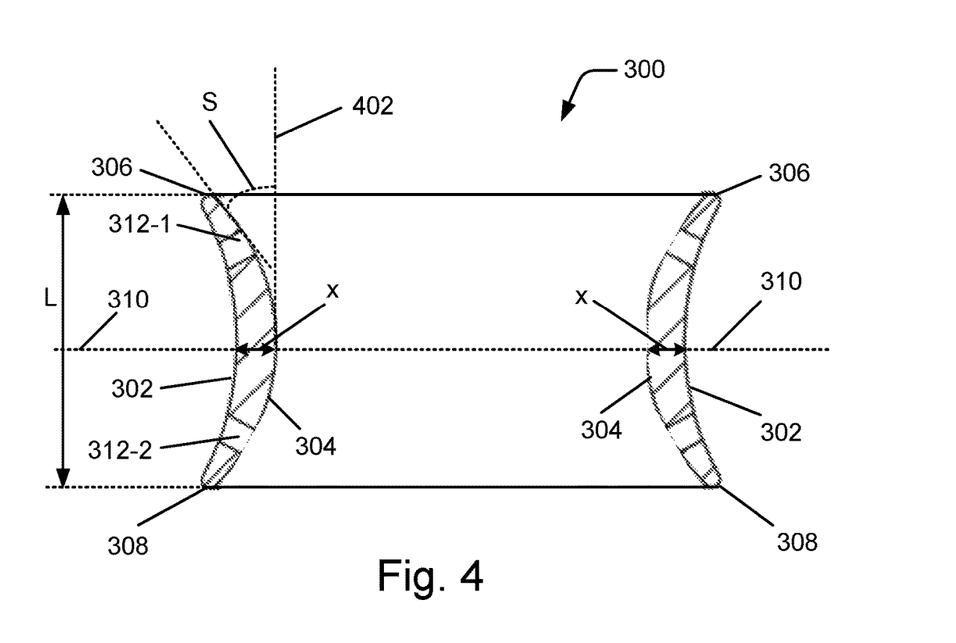
FIG. 4 illustrates a cross-sectional view of the suturing ring of FIG. 3, in accordance with an example implementation of the present subject matter.

The suturing ring may be symmetrical or asymmetrical about the mid-circumferential plane. FIG. 3 and FIG. 4 illustrate the symmetrical suturing ring, in which the mid-circumferential plane divides the suturing ring into two symmetrical halves. The asymmetrical suturing ring is illustrated and described through FIG. 8.

In an example implementation, the inner surface 304 has a continuously increasing slope from the mid-circumferential plane towards the top peripheral edge 306 and the bottom peripheral edge 308. Thus, the inner diameter of the suturing ring 300 gradually increases from the mid-circumferential plane towards the top peripheral edge 306 and the bottom peripheral edge 308. The inner surface 304 may have an angle of slope at the top peripheral edge 306 and at the bottom peripheral edge 308 in a range from about 10 degrees to about 80 degrees. The inner diameter of the suturing ring 300 at the mid-circumferential plane may be in a range from about 12 mm to about 32 mm and the inner diameter of the suturing ring 300 at the top peripheral edge 306 and at the bottom peripheral edge 308 may be in a range from about 15 mm to about 35 mm. For example, in small prosthetic valves, such as prosthetic valves for infants, the suturing ring 300 may have an outer diameter of about 19 mm and an average inner diameter of about 16.5 mm. This also results in an increase of about 30% in the effective orifice area of the prosthetic valve having the suturing ring 300.

In an example implementation, the suturing ring 300 has a variable annular thickness. The annular thickness may be defined as a distance between the inner surface 304 and the outer surface 302 of the suturing ring 300. The annular thickness may vary in a direction perpendicular to the radial direction of the suturing ring 300. In an example implementation, the annular thickness of the suturing ring 300 reduces continuously from the mid-circumferential plane towards the top peripheral edge 306 and the bottom peripheral edge 308. The annular thickness at the mid-circumferential plane ranges from about 0.45 mm to about 1.5 mm. The suturing ring 300 may have a plurality of suture-receiving passages.

FIG. 3 shows suture-receiving passages 312-1 between the mid-circumferential plane boundary 310 and the top peripheral edge 306 and suture-receiving passages 312-2 between the mid-circumferential plane boundary 310 and the bottom peripheral edge 308. The plurality of suture-receiving passages may be collectively referred to as suture-receiving passages 312. The suture-receiving passages 312 pass from the inner surface 304 to the outer surface 302. In an example implementation, the suture-receiving passages 312 may be through-holes running from the inner surface 304 to the outer surface 302. Suture-threads may be passed through the suture-receiving passages 312. The suture-threads enable stitching the prosthetic valve to the native human tissue at the position of implant of the prosthetic valve, such as the aortic annulus, lying between the aorta and the left ventricle of the human heart.

FIG. 4 illustrates a cross-sectional view of the suturing ring 300 for the prosthetic heart valve, in accordance with an example implementation of the present subject matter. The suturing ring 300, as shown, is symmetrical about the mid-circumferential plane. In the cross-sectional view of the suturing ring 300, the curved line referenced as 304 represents the inner surface of the suturing ring 300, and the curved line referenced as 302 represents the outer surface of the suturing ring 300. As shown in FIG. 4, the inner surface 304 and the outer surface 302 meet at the top peripheral edge 306 and the bottom peripheral edge 308 of the suturing ring 300. FIG. 4 also shows the boundary 310 of the mid-circumferential plane that passes through the mid-point of the linear distance L between the top peripheral edge 306 and the bottom peripheral edge 308, where the annular thickness of the suturing ring 300 is maximum.

As can be seen from FIG. 4, the suturing ring 300 has an arcuate profile, where the annular thickness of the suturing ring 300 is maximum (represented by 'x') at the mid-circumferential plane and reduces continuously from the mid-circumferential plane towards the top peripheral edge 306 and the bottom peripheral edge 308. The variable annular thickness of the suturing ring 300 eliminates any sudden or abrupt obstruction in the flow path of blood, while the blood enters or exits the prosthetic valve at the bottom peripheral edge 308 and the top peripheral edge 306. This allows blood flowing through the prosthetic heart valve to maintain a hemodynamic flow pattern that minimizes turbulence and platelet activation.

As mentioned earlier, the inner surface 304 of the suturing ring 300 may have a continuously increasing slope from the boundary 310 of the mid-circumferential plane towards the top peripheral edge 306 and the bottom peripheral edge 308. In an example implementation, the angle of slope S subtended by the inner surface 304 at the top peripheral edge 306 with a line 402 perpendicular to the mid-circumferential plane boundary 210 is in a range from about 10 degrees to about 80 degrees. In an example implementation, the angle of slope S subtended by the inner surface 304 at the top peripheral edge 306 and the bottom peripheral edge 308 may be the same, as the suturing ring 300 is symmetrical about the mid-circumferential plane.

Figure 5:
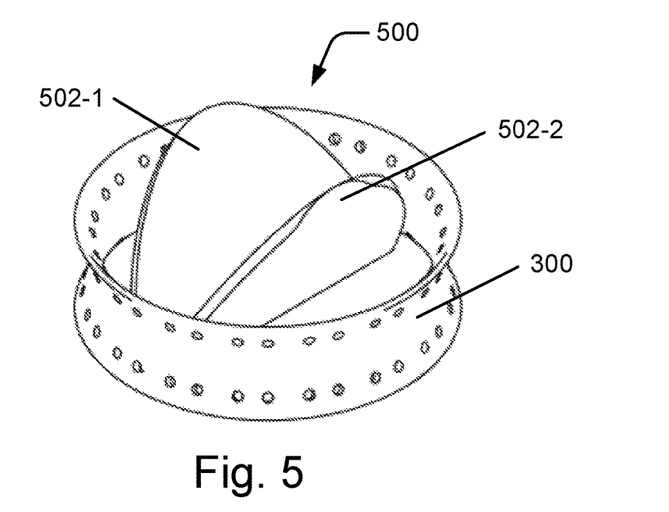
FIG. 5 illustrates a perspective view of the prosthetic valve with the suturing ring of FIG. 3, in accordance with an example implementation of the present subject matter.

FIG. 5 illustrates a perspective view of the prosthetic valve 500, hereinafter referred to as the valve 500, with the suturing ring 300 in accordance with an example implementation of the present subject matter. As shown in FIG. 5 the suturing ring 300 forms the housing of the prosthetic valve 500. In said example, the valve 500 has two leaflets 502-1 and 502-2, hereinafter collectively referred to as leaflets 502, mounted within the suturing ring 300. The leaflets 502 have struts (not shown in FIG. 5) through which the leaflets 502 can be mounted on the suturing ring 300. The leaflets 502 can rotate about the struts to move between an open and a closed position thereby regulating the flow of blood through the valve 500.

The leaflets 502 and the suturing ring 300 of the valve 500 may be formed from one of pyrolytic carbon deposited on graphite, pyrolytic carbon-silicon, and biocompatible metals such as titanium. Pyrolytic carbon is resistant to wear and tear, and has high strength and durability. Pyrolytic carbon is also highly resistant to blood clotting and causes little damage to blood cells thereby allowing natural blood flow through the valve 500. As Pyrolytic carbon is resistant to cracks and fatigue, it allows flexibility in design of the valve 500. Alternatively, in an example implementation, biocompatible polymers or other biocompatible metals may also be used for the suturing ring 300 and the leaflets 502.

Figure 6:
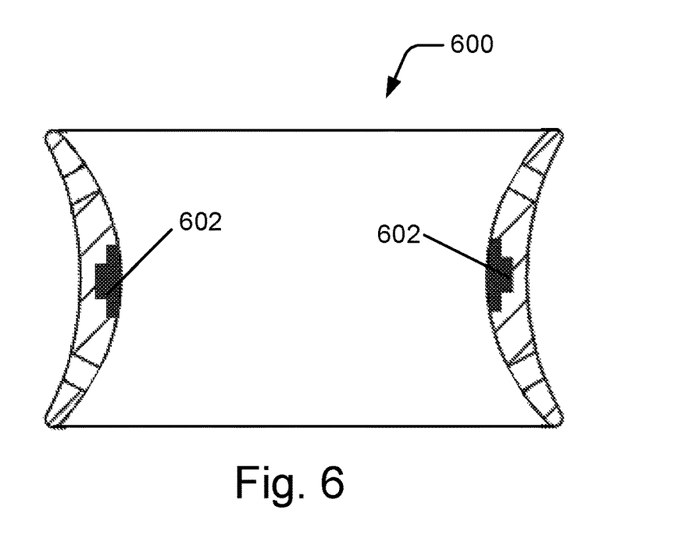
FIG. 6 illustrates a cross-sectional view of the suturing ring depicting rails for mounting of leaflets, in accordance with an example implementation of the present subject matter.

FIG. 6 illustrates a cross-sectional view of the suturing ring 600 depicting a channel 602 for mounting of leaflets, in accordance with an example implementation of the present subject matter. The channel 602 runs continuously throughout the inner surface along the mid-circumferential plane of the suturing ring 600. The leaflets are mounted within the suturing ring 600 by positioning the struts of the leaflets in the channel 602. The leaflets can be rotated about a vertical axis perpendicular to the mid-circumferential plane of the suturing ring 600 by moving the struts within the channel 602 along the circumference of the inner surface of the suturing ring 600. As a result, the orientation of the leaflets within the suturing ring 600 of the prosthetic valve can be changed during implantation of the prosthetic valve.

Figure 7:
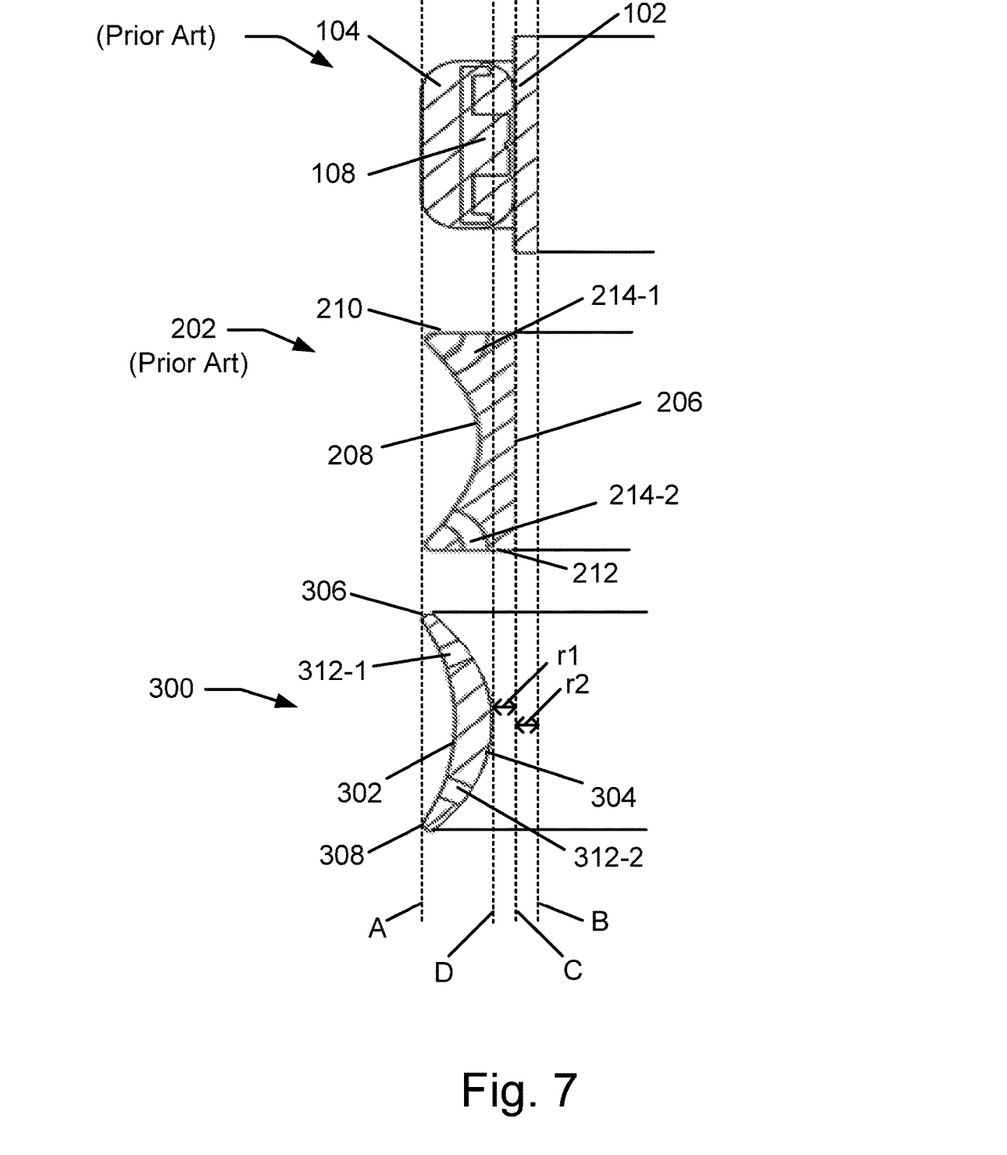
FIG. 7 illustrates a comparative view of a cross-sectional portion of the housing and fabric layer of the conventional prosthetic heart valve as illustrated in FIG. 1a, a cross-sectional portion of the conventional suturing ring of the conventional prosthetic heart valve as illustrated in FIG. 2a, and the suturing ring of the prosthetic heart valve illustrated in FIG. 5.

FIG. 7 illustrates a comparative view of a cross-sectional portion of the housing 102 and the fabric layer 104 of the conventional prosthetic heart valve 100 as illustrated in FIG. 1a, a cross-sectional portion of the conventional suturing ring 202 of the conventional prosthetic heart valve 200 as illustrated in FIG. 2a, and the suturing ring 300 of the prosthetic heart valve 500 as illustrated in FIG. 5. In FIG. 7, effective thickness of the housing 102 and the fabric layer 104 is denoted by the distance between the lines A and B, effective thickness of the conventional suturing ring 202 is denoted by the distance between the lines A and C, and effective thickness of the suturing ring 300 is denoted by the distance between the lines A and D.

As can be seen from FIG. 7, the conventional suturing ring 202 as well as the suturing ring 300 of the present subject matter have suture-receiving passages for stitching the valve to the native tissue. The suture-receiving passage 214-1, 214-2 in the conventional suture ring 202 and the suture-receiving passage 312-1, 312-2 in the suturing ring 300 may have the same pre-defined diameter. In an example implementation, the pre-defined diameter may be in a range from about 0.6 mm to 1.1 mm which has to be maintained in order to allow passage of surgical needle and suture-threads through the suture-receiving passage. In order to enable drilling of suture-receiving passages 214 of the pre-defined diameter, the conventional suturing ring 202 has to maintain a considerable effective thickness at the top end surface 210 and the bottom end surface 212 (denoted by the distance between the lines A and C). In an example implementation, the effective thickness at the top end surface 210 and the bottom end surface 212 of the conventional suturing ring 202 may range between 2 mm to 3 mm so that the suture-receiving passages 214 can be drilled without any fracture or damage to the conventional suture ring 202. This is not the case with the suturing ring 300 of the present subject matter.

In the suturing ring 300, the suture-receiving passage 312 passes from an inner surface 304 to an outer surface 302. This design of the suture-receiving passage 312 eliminates the need of having planar top and bottom surfaces, such as the top end surface 210 and bottom end surface 212 of the conventional suturing ring 202, in the suturing ring 300. Thus, the effective thickness of the suturing ring 300 (denoted by the distance between the lines A and D) is lesser as compared to the effective thickness of the conventional suturing ring 202 (denoted by the distance between the lines A and C). The reduction in effective thickness of the suturing ring 300 is denoted by 'r1' mm in FIG. 7. This results in an increase in the inner diameter at the mid-circumferential plane of the suturing ring 300 by 2 times 'r1' mm as compared to the inner diameter of the conventional suturing ring 200. The increase in the inner diameter of the suturing ring 300 provides a greater effective orifice area for blood flow through the prosthetic valve 500 having the suturing ring 300 as compared to the effective orifice area for the valve 200. Thus, the effective orifice area, which may be understood as the area available for blood flow through the prosthetic valve of the present subject matter increases without any modification/increment in the overall size of the valve housing thereby reducing chances of medical conditions, such as left ventricle hypertrophy.

Also, it would be appreciated from FIG. 7 that the effective thickness of the fabric layer 104 and the housing 102 (denoted by the distance between the lines A and B) puts substantial limitation on the inner diameter of the valve 100, as the outer diameter is substantially fixed. The suturing ring 300 of the present subject matter does not use a fabric layer to stitch the valve 500 to the native tissue. Thus, the effective thickness of the suturing ring 300 (denoted by the distance between the lines A and D) is lesser as compared to the effective thickness of the fabric layer 104 along with the housing 102 (denoted by the distance between the lines A and B). The reduction in the effective thickness of the suturing ring 300 is denoted by 'r1+r2' mm in FIG. 7. This results in an increase in the inner diameter at the mid-circumferential plane of the suturing ring 300 by 2 times 'r1+r2' mm as compared to the inner diameter of the valve 100. Thus, the valve 500 having the suturing ring 300 has a larger effective orifice area as compared to the effective orifice area of the valve 100 and the valve 200 thereby reducing chances of medical complications post-implant.

Figure 8:
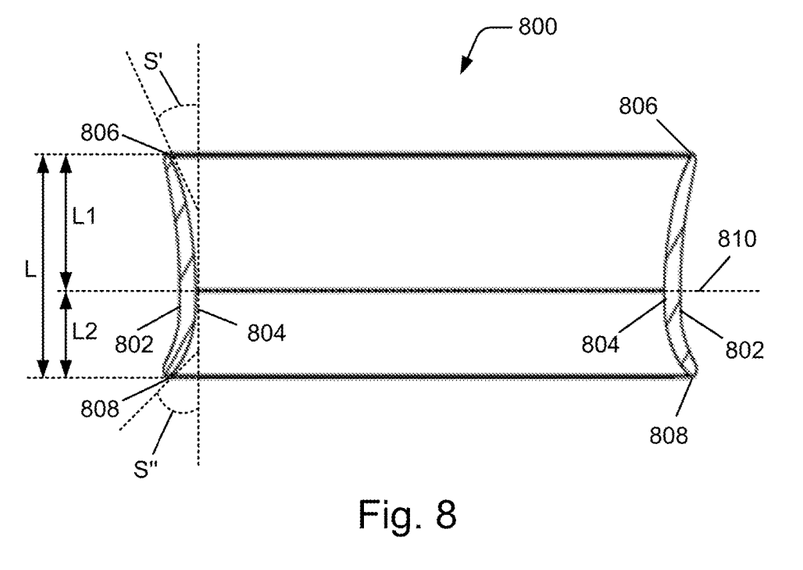
FIG. 8 illustrates a cross-sectional view of a suturing ring for the prosthetic heart valve, in accordance with an example implementation of the present subject matter.

FIG. 8 illustrates a cross-sectional view of a suturing ring 800 for a prosthetic heart valve, in accordance with an example implementation of the present subject matter. The suturing ring 800, as shown, is asymmetrical about the mid-circumferential plane. An asymmetrical suture ring can provide superior flow performance compared to a symmetrical suture ring for certain prosthetic valve applications. Although the valve 500 is shown with the symmetrical suturing ring 300, the asymmetrical suturing ring 800 can also be used for the valve as another example. It may be noted the suturing ring 800 has suture-receiving passages (not shown), similar to the suture-receiving passages 312 shown with the suturing ring 300.

The curved line referenced as 804 represents the inner surface of the suturing ring 800, and the curved line referenced as 802 represents the outer surface of the suturing ring 800. As shown in FIG. 8, the inner surface 804 and the outer surface 802 meet at the top peripheral edge 806 and the bottom peripheral edge 808 of the suturing ring 800. FIG. 8 also shows a boundary 810 of the mid-circumferential plane where the thickness of the suturing ring 800 is maximum. The boundary 810 of the mid-circumferential plane passes through a point at a linear distance L1 from the top peripheral edge 806 and at a linear distance L2 from the bottom peripheral edge 808. The annular thickness of the suturing ring 800 at the mid-circumferential plane ranges from about 0.45 mm to about 1.5 mm.

In an example implementation, the top peripheral edge 806 and the bottom peripheral edge 808 may be separated by a linear distance denoted by L in FIG. 8. The linear distance L shown in FIG. 8 is similar to that shown in FIG. 4, and may be understood to be the shortest distance between the top peripheral edge 806 and the bottom peripheral edge 808. The linear distance L maybe in a range from about 4.5 mm to about 10.5 mm. It may be noted that for the suturing ring 800 the linear distance L1, between the top peripheral edge 806 and the mid-circumferential plane, and the linear distance L2, between the bottom peripheral edge 808 and the mid-circumferential plane, are different with respect to each other.

Further, as shown, the inner surface 804 of the suturing ring 800 at the top peripheral edge 806 has an angle of slope S' with the vertical line, and the inner surface 804 of the suturing ring 800 at the bottom peripheral edge 808 has an angle of slope S" with the vertical line. In an example implementation, the angle of slope S' and the angle of slope S" are in a range from about 10 degrees to about 80 degrees. It may be noted that for the suturing ring 800 the angle of slope S' and the angle of slope S" are different with respect to each other. The other dimensions of the suturing ring 800 may be same as those mentioned earlier with respect to the suturing ring 300.

The asymmetric suturing ring 800 provides different profiles at the outlet and the inlet of the prosthetic heart valve. Different profiles at the inlet and the outlet of the prosthetic heart valve provide optimized flow dynamics to the fluid flowing through the prosthetic heart valve.

Although implementations for a suturing ring are described, it is to be understood that the present subject matter is not necessarily limited to the specific features described herein. Rather, the specific features are disclosed as example implementations of the suturing attachment.

We claim:

1. A suturing ring for a prosthetic heart valve, wherein the suturing ring has a variable annular thickness reducing continuously from a mid-circumferential plane of the suturing ring towards a top peripheral edge and a bottom peripheral edge of the suturing ring, wherein the suturing ring has an inner surface and an outer surface meeting at the top peripheral edge and the bottom peripheral edge, the inner surface having a continuously increasing slope from the mid-circumferential plane towards the top peripheral edge and the bottom peripheral edge, wherein the suturing ring comprises a plurality of suture-receiving passages from the inner surface to the outer surface, and wherein the suturing ring is asymmetrical about the mid-circumferential plane.

2. The suturing ring as claimed in claim 1, wherein the inner surface of the suturing ring at the top peripheral edge and the bottom peripheral edge has an angle of slope in a range from about 10 degrees to about 80 degrees.

3. The suturing ring as claimed in claim 1, wherein the suturing ring forms a valve housing of the prosthetic heart valve.

4. The suturing ring as claimed in claim 1, wherein the suturing ring at the mid-circumferential plane has an annular thickness in a range from about 0.45 mm to about 1.5 mm.

5. The suturing ring as claimed in claim 1, wherein the suturing ring at the mid-circumferential plane has an inner diameter in a range from about 12 mm to about 32 mm.

6. The suturing ring as claimed in claim 1, wherein the suturing ring at the top peripheral edge and the bottom peripheral edge has an inner diameter in a range from about 15 mm to about 35 mm.

7. The suturing ring as claimed in claim 1, wherein the top peripheral edge and the bottom peripheral edge are separated by a linear distance in a range from about 4.5 mm to about 10.5 mm.

8. A prosthetic heart valve comprising:
   a valve housing; and
   at least one leaflet mounted on a strut attached to the valve housing, such that the at least one leaflet may rotate about the stmt to control the flow of blood through the prosthetic heart valve,
   wherein the valve housing comprises:
   a suturing ring for securing the prosthetic heart valve to native tissue, wherein the suturing ring has a variable annular thickness reducing continuously from a mid-circumferential plane of the suturing ring towards a top peripheral edge and a bottom peripheral edge of the suturing ring, wherein the suturing ring has an inner surface and an outer surface meeting at the top peripheral edge and the bottom peripheral edge, wherein the inner surface has a continuously increasing slope from the mid-circumferential plane towards the top peripheral edge and the bottom peripheral edge, the suturing ring having a plurality of suture-receiving passages from the inner surface to the outer surface, wherein the suture-receiving passages guide suture-threads to attach the suturing ring to human tissues surrounding the suturing ring, and wherein the suturing ring is asymmetrical about the mid-circumferential plane.

* * * * *